(12) United States Patent
Inuga et al.

(10) Patent No.: US 7,742,572 B2
(45) Date of Patent: Jun. 22, 2010

(54) X-RAY IMAGING APPARATUS AND X-RAY IMAGING METHOD

(75) Inventors: Miho Inuga, Kawasaki (JP); Takashi Yoshida, Miura (JP)

(73) Assignee: Canon Kabushiki Kaisha, Tokyo (JP)

( * ) Notice: Subject to any disclaimer, the term of this patent is extended or adjusted under 35 U.S.C. 154(b) by 193 days.

(21) Appl. No.: 12/099,580

(22) Filed: Apr. 8, 2008

(65) Prior Publication Data

US 2008/0317205 A1    Dec. 25, 2008

(30) Foreign Application Priority Data

May 7, 2007    (JP) ............................. 2007-122802

(51) Int. Cl.
*H05G 1/38* (2006.01)

(52) U.S. Cl. ..................................... 378/108

(58) Field of Classification Search .................. 378/96, 378/97, 108
See application file for complete search history.

(56) References Cited

U.S. PATENT DOCUMENTS

| | | | | |
|---|---|---|---|---|
| 5,966,425 | A * | 10/1999 | Beland | 378/108 |
| 2002/0191741 | A1 | 12/2002 | Brendler et al. | 378/96 |
| 2006/0115039 | A1 * | 6/2006 | Gohno | 378/4 |
| 2007/0036272 | A1 * | 2/2007 | Johansson et al. | 378/108 |
| 2008/0159481 | A1 | 7/2008 | Yoshida | 378/95 |
| 2009/0041200 | A1 * | 2/2009 | Lu et al. | 378/152 |

FOREIGN PATENT DOCUMENTS

| | | |
|---|---|---|
| JP | 2005-253801 A1 | 9/2005 |
| WO | WO 2005/051198 A1 | 6/2005 |
| WO | WO 2006/085247 A2 | 8/2006 |

* cited by examiner

*Primary Examiner*—Chih-Cheng G Kao
(74) *Attorney, Agent, or Firm*—Fitzpatrick, Cella, Harper & Scinto (57) ABSTRACT

In a X-ray imaging apparatus an estimation unit estimates a cumulative exposure dose of X-rays irradiated onto an object, and a remaining exposure tolerance dose calculation unit calculates a remaining exposure tolerance dose using a difference between a tolerated maximum exposure dose and the cumulative exposure dose. A X-ray irradiation tolerance period calculation unit calculates an X-ray irradiation tolerance period using a difference between a predetermined scheduled X-ray irradiation period and an actual irradiation period of X-rays irradiated onto the object, an X-ray irradiation reference dose calculation unit calculates reference dose per unit time that will form a basis for irradiation based on the remaining exposure tolerance dose and the X-ray irradiation tolerance period, and a control unit that controls X-ray irradiation of the object by setting dose per unit time within the X-ray irradiation tolerance period based on the reference dose.

4 Claims, 11 Drawing Sheets

X-RAY IMAGING APPARATUS AND X-RAY IMAGING METHOD

BACKGROUND OF THE INVENTION

1. Field of the Invention

The present invention relates to an X-ray imaging technique for preventing patients from being exposed to excessive doses of radiation.

2. Description of the Related Art

X-ray diagnostic imaging utilizing X-rays has typically been applied in radiographic interpretation using still images, although in recent years its application has expanded to include X-ray fluoroscopic examination and surgical support. However, X-ray fluoroscopic examination and surgical support, while being extremely beneficial, unavoidably expose patients to radiation, and the exposure risk must always be taken into consideration when performing X-ray diagnosis and surgical support. Despite these risks, the X-ray dose has heretofore typically been adjusted manually by the operator providing the medical care. The operator selects the appropriate X-ray dose, with regard to the surgical objective, examination application, examination site, the patient's physique, age and sex, the characteristics of the apparatus and so on. In the case of a procedure using fluorography, the operator prepares a surgical plan after manually calculating the X-ray dose.

Japanese Patent Laid-Open No. 2005-253801 proposes an X-ray diagnostic apparatus that estimates the cumulative exposure dose, and issues a warning and stops the irradiation when the estimated cumulative exposure dose reaches a prescribed limit. Further, Japanese Patent Laid-Open No. 2005-253801 proposes an X-ray diagnostic apparatus that estimates the cumulative exposure dose, works out the period for which irradiation is possible at the current X-ray irradiation dose per unit time based on the estimated cumulative exposure dose, and displays the result.

Overexposure can be avoided with conventional X-ray diagnostic apparatus that estimates the cumulative exposure dose, and issues a warning and stops the irradiation when the cumulative exposure dose reaches a prescribed dose. On the other hand, however, the scheduled procedure has to be aborted even though it may not have been completed. Even if the cumulative exposure dose is estimated and the period for which irradiation is possible at the current X-ray irradiation dose per unit time is worked out based on the cumulative exposure dose and displayed, the procedure either needs to be aborted or continued for longer than the displayed remaining period if the procedure has not ended within the remaining period.

SUMMARY OF THE INVENTION

The present invention has been made in consideration of the above problems, and has as its object to provide an X-ray imaging technique that enables X-ray irradiation to be continued until a time period set by an operator has elapsed, while at the same time inhibiting excessive X-ray irradiation.

According to one aspect of the present invention, there is provided an X-ray imaging apparatus comprising: an estimation unit adapted to estimate a cumulative exposure dose of X-rays irradiated onto an object; a remaining exposure tolerance dose calculation unit adapted to calculate a remaining exposure tolerance dose, using a difference between a tolerated maximum exposure dose and the cumulative exposure dose; an X-ray irradiation tolerance period calculation unit adapted to calculate an X-ray irradiation tolerance period, using a difference between a predetermined scheduled X-ray irradiation period and an actual irradiation period of X-rays irradiated onto the object; an X-ray irradiation reference dose calculation unit adapted to calculate an X-ray irradiation reference dose per unit time that will form a basis of X-ray irradiation, based on the remaining exposure tolerance dose and the X-ray irradiation tolerance period; and a control unit adapted to control X-ray irradiation onto the object by setting an X-ray irradiation dose per unit time within the X-ray irradiation tolerance period, based on the X-ray irradiation reference dose.

According to another aspect of the present invention, there is provided an X-ray imaging apparatus comprising: an X-ray generation unit for generating X-rays; an acquiring unit adapted to acquire a cumulative value of an irradiation dose of X-rays irradiated onto a subject; and a control unit adapted to control an X-ray irradiation dose per unit time of the X-ray generation unit generating the X-rays, so that the cumulative value acquired by the acquiring unit reaches a target value in a predetermined period.

According to still another aspect of the present invention, there is provided an X-ray imaging method comprising: acquiring a cumulative value of an irradiation dose of X-rays irradiated onto a subject; and controlling an X-ray irradiation dose per unit time of an X-ray generation unit generating the X-rays, so that the cumulative value acquired in the acquisition step reaches a target value in a predetermined period.

The present invention enables X-ray irradiation to be continued until a time period set by an operator has elapsed, while at the same time inhibiting excessive X-ray irradiation.

Further features of the present invention will become apparent from the following description of exemplary embodiments (with reference to the attached drawings).

DESCRIPTION OF THE EMBODIMENTS

Exemplary preferred embodiments of the present invention will now be described in detail with reference to the drawings. The constituent elements described in these embodiments are merely by way of example, and, moreover, the technical scope of the invention is defined by the claims and is not limited by the following individual embodiments.

First Embodiment

Configuration of X-ray Imaging Apparatus

Figure 1:
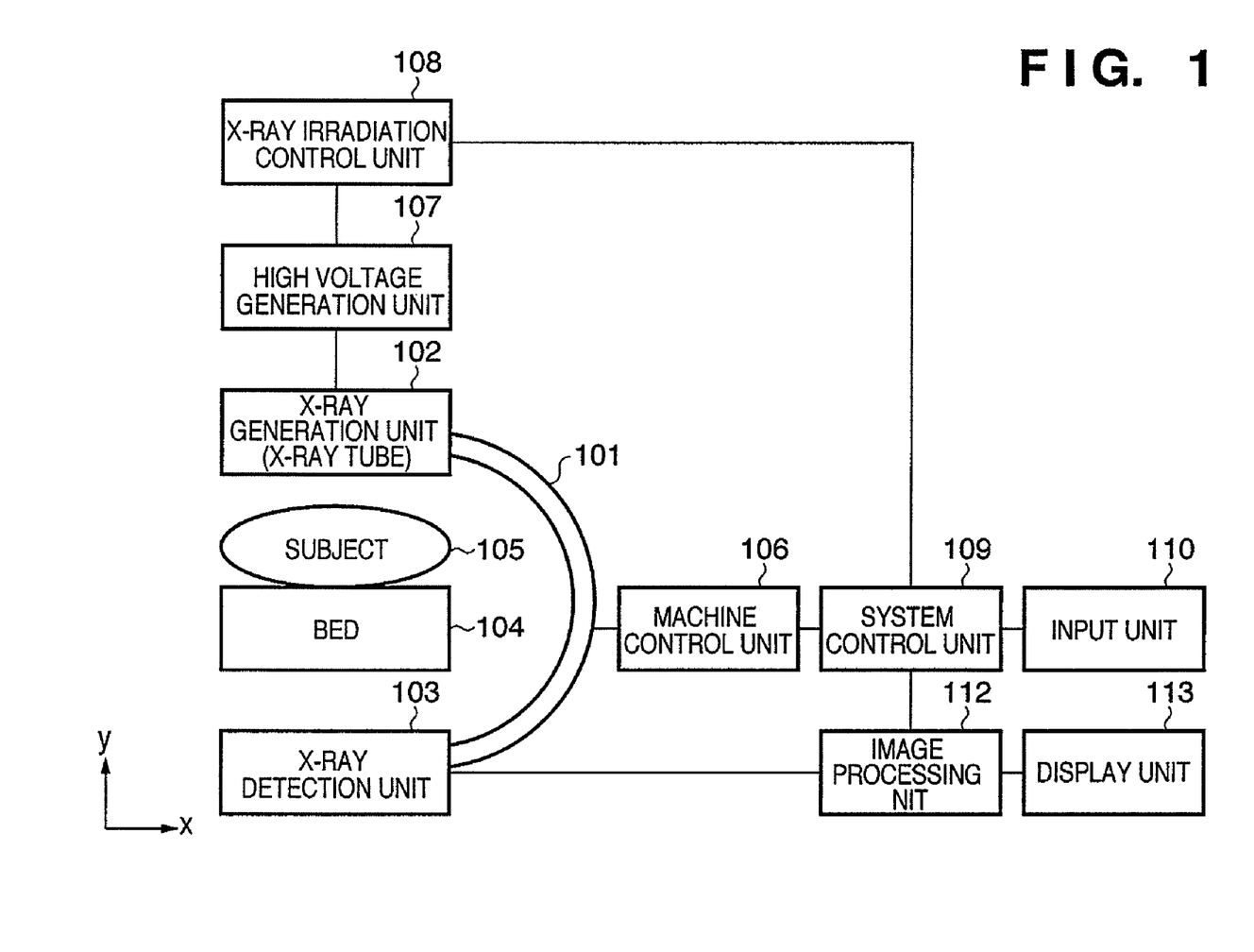
FIG. 1 shows the configuration of an X-ray imaging apparatus according to embodiments of the present invention.

FIG. 1 shows an example of the configuration of an X-ray imaging apparatus according to the present invention. An X-ray generation unit (X-ray tube) 102 is an X-ray generation source that irradiates X-rays onto a subject (object) 105. The X-ray generation unit (X-ray tube) 102 is held by one end of a holding unit 101. An X-ray detection unit 103 is a sensor that detects X-rays irradiated from the X-ray generation unit (X-ray tube) 102. The X-ray detection unit 103 is held by the other end of the holding unit 101. The X-ray detection unit 103 and the X-ray generation unit (X-ray tube) 102 are held facing one another by the holding unit 101. Note that apart from being fixed, the X-ray detection unit 103 and the X-ray generation unit (X-ray tube) 102 may be held in a state where they are movable relative to one another, provided they continue to face one another.

A bed 104 is provided between the X-ray generation unit (X-ray tube) 102 and the X-ray detection unit 103. The bed 104 is provided with a top board (not shown) and a leg portion (not shown) supporting the top board, and the subject (object) 105, that is, the patient, is mounted on the top board. The top board is movable in a required direction, such as vertically (y direction in FIG. 1) and horizontally (x direction in FIG. 1), for example.

The holding unit 101 and the top board (not shown) of the bed 104 are respectively mounted with a drive motor (not shown) and a position sensor (not shown) for position detection, and the motors and position sensors are controlled by a machine control unit 106.

The machine control unit 106 can control the position of the holding unit 101 and the top board of the bed 104 by driving the motors based on the sensor information of the position sensors. The holding unit 101 and the top board of the bed 104 are positioned so as to be in a prescribed positional relation, under the control of the machine control unit 106.

The X-ray generation unit 102, which is connected to a high voltage generation unit 107, receives a prescribed voltage generated by the high voltage generation unit 107 and irradiates X-rays toward the subject (object) 105. An X-ray irradiation control unit 108 can control the X-ray dose irradiated from the X-ray generation unit 102 when imaging is performed, by controlling the high voltage generation unit 107.

A system control unit 109 integrally controls the machine control unit 106 and the X-ray irradiation control unit 108. An image processing unit 112 performs image processing on image data read out from the X-ray detection unit 103. The system control unit 109 controls the image processing unit 112 so as to perform image processing such as gamma correction and noise reduction on image data read out from the X-ray detection unit 103.

A display unit 113 displays image data processed by the image processing unit 112, information (name, age, sex, height, weight, imaging target site, etc.) on the subject (object), and imaging conditions including X-ray conditions.

An input unit 110 can receive input of X-ray conditions, information on the subject (object) and the like as control input to the system control unit 109, the machine control unit 106 and the X-ray irradiation control unit 108. The input unit 110 is constituted, for example, by a keyboard, a mouse, a touch panel, a membrane button, a joystick, and an irradiation switch and a foot pedal for triggering irradiation start and stop. An X-ray irradiation dose, a minimum X-ray irradiation dose per unit time required to perform a procedure, a tolerated maximum exposure dose, and a scheduled X-ray irradiation period are input from the input unit 110. Imaging conditions, information (name, age, sex, height, weight, imaging target site, etc.) on the subject (object), information on the operator and the like are further input from the input unit 110.

Functional Configuration of System Control Unit 109

Figure 2:
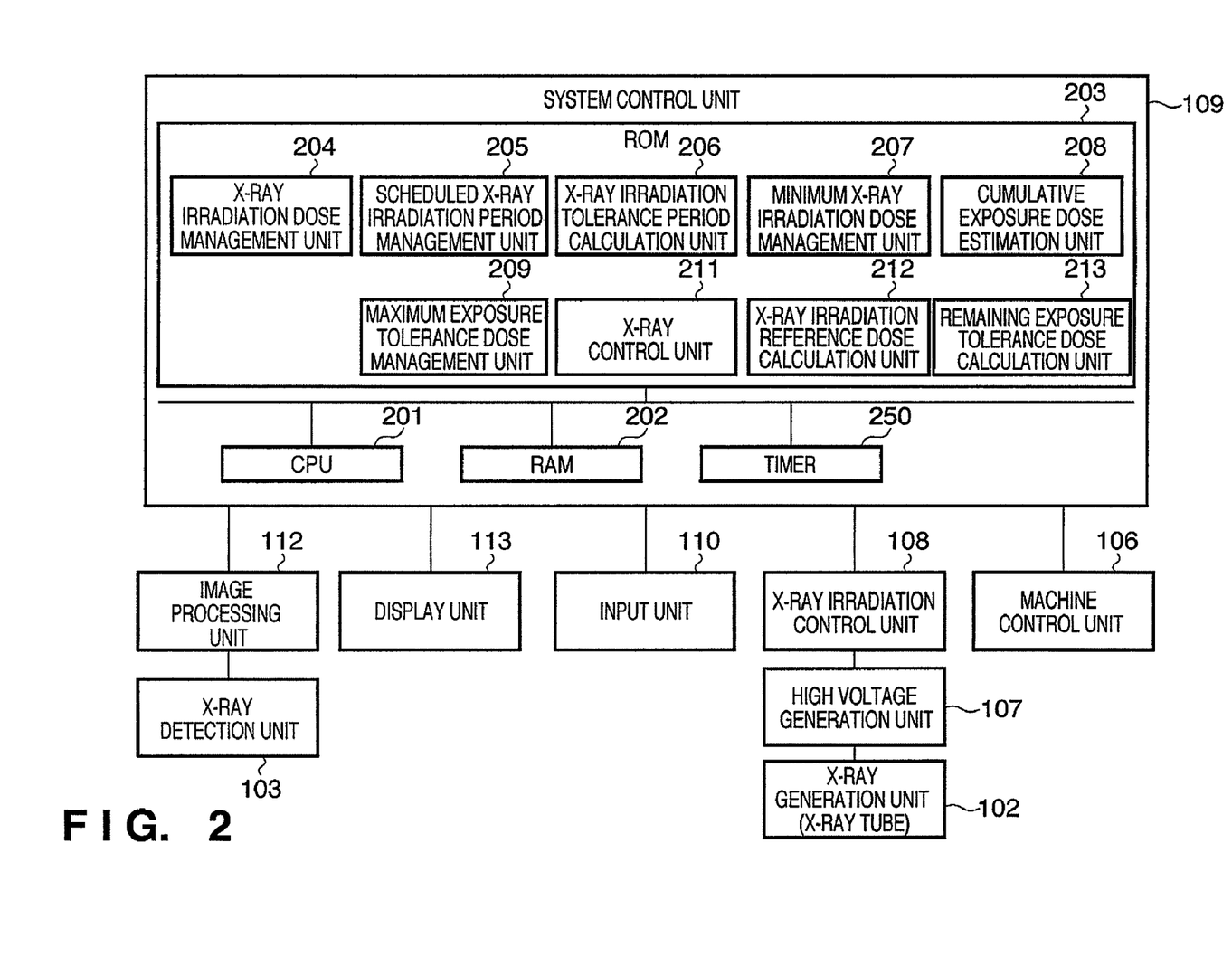
FIG. 2 is a block diagram showing a functional configuration of a system control unit 109.

FIG. 2 is a block diagram showing a functional configuration of the system control unit 109.

The system control unit 109 is constituted by a CPU 201 that realizes the steps of the flowcharts described below, a RAM 202 that functions as a main memory of the CPU, a work area and the like, and a ROM 203 that stores computer programs. The RAM 202 and the ROM 203 are computer readable memories. A timer 250 can measure the X-ray irradiation period. Based on the measurement result of the timer 250, the CPU 201 is able to control the duration of X-ray irradiation and the execution timing of programs stored in the ROM 203, which will be described below.

The ROM 203 stores programs for the CPU 201 to execute the functions of an X-ray irradiation dose management unit 204, a scheduled X-ray irradiation period management unit 205, an X-ray irradiation tolerance period calculation unit 206, and a minimum X-ray irradiation dose management unit 207.

The ROM 203 further stores programs for the CPU 201 to execute the functions of a cumulative exposure dose estimation unit 208, a maximum exposure tolerance dose management unit 209, an X-ray control unit 211, an X-ray irradiation reference dose calculation unit 212, and a remaining exposure tolerance dose calculation unit 213.

The X-ray irradiation dose management unit 204 can manage an X-ray irradiation dose per unit time (i.e. flux) irradiated onto the subject (object) 105, and stores information related to the X-ray irradiation dose per unit time in a storage unit such as a memory or a hard disk. The scheduled X-ray irradiation period management unit 205 can manage a scheduled X-ray irradiation period for a procedure, using a method such as storage in a storage unit.

The minimum X-ray irradiation dose management unit 207 can manage a minimum X-ray irradiation dose per unit time (flux) required to perform a procedure, using a method such as storage in a storage unit. The X-ray control unit 211 can control the X-ray irradiation control unit 108 based on the X-ray irradiation dose per unit time managed by the X-ray irradiation dose management unit 204, and the imaging conditions, information on the subject and the like input from the input unit 110.

The cumulative exposure dose estimation unit 208 estimates the cumulative exposure dose after normalizing factors (tube voltage, mAs, filtration, FSD, apparatus, etc.) that affect the X-ray irradiation dose per unit time to a certain value, and transforming the normalized factors into coefficients. The maximum exposure tolerance dose management unit 209 can manage a tolerated maximum X-ray exposure dose, using a method such as storage in a storage unit.

The X-ray irradiation tolerance period calculation unit 206 has a function of computing an X-ray irradiation tolerance period obtained by subtracting the irradiation period for which the subject (object) has actually be irradiated from the scheduled X-ray irradiation period held by the scheduled X-ray irradiation period management unit 205.

An X-ray irradiation tolerance period $T1$ is given by the following equation (1), where $T4$ is the scheduled X-ray irradiation period held by the scheduled X-ray irradiation period management unit 205, and T0 is the irradiation period for which the subject (object) has actually been irradiate:

$$T1 = T4 - T0 \quad (1)$$

The remaining exposure tolerance dose calculation unit 213, which functions as a remaining exposure tolerance dose computation unit, computes a remaining exposure tolerance dose obtained by subtracting the cumulative exposure dose computed by the cumulative exposure dose estimation unit 208 from the maximum exposure dose tolerated by the maximum exposure tolerance dose management unit 209.

A remaining exposure tolerance dose E2 is given by the following equation (2), where E3 is the maximum exposure tolerance dose held by the maximum exposure tolerance dose management unit 209, and E1 is the cumulative exposure dose estimated by the cumulative exposure dose estimation unit 208:

$$E2 = E3 - E1 \quad (2)$$

The X-ray irradiation reference dose calculation unit 212 computes, as an X-ray irradiation reference dose, a constant X-ray irradiation dose per unit time at which the cumulative exposure dose will equal the remaining exposure tolerance dose in the case where irradiation at a constant X-ray irradiation dose per unit time is continued for the duration of the X-ray irradiation tolerance period, based on the remaining exposure tolerance dose and the X-ray irradiation tolerance period.

The cumulative exposure dose (E) where a prescribed X-ray irradiation dose (x) is irradiated for a prescribed period (t) can be represented by E=f(t, x). At this time, the X-ray irradiation reference dose calculation unit 212 computes an X-ray irradiation reference dose (x1) per unit time that satisfies equation (3), where T1 is the X-ray irradiation tolerance period, E2 is the tolerated remaining exposure dose, and x1 is the X-ray irradiation reference dose per unit time:

$$E2 = f(T1, x1) \quad (3)$$

The X-ray control unit 211 can control the X-ray irradiation dose, based on the relation between the X-ray irradiation reference dose (x1) per unit time computed by the X-ray irradiation reference dose calculation unit 212 and the minimum X-ray irradiation dose per unit time managed by the minimum X-ray irradiation dose management unit 207. Further, the X-ray control unit 211 controls the X-ray irradiation dose per unit time, based on the relation between the X-ray irradiation reference dose (x1) per unit time computed by the X-ray irradiation reference dose calculation unit 212 and the X-ray irradiation dose per unit time managed by the X-ray irradiation dose management unit 204.

Here, the X-ray irradiation dose per unit time, the scheduled X-ray irradiation period, the maximum exposure tolerance dose, and the minimum X-ray irradiation dose per unit time can be set from the input unit 110. The X-ray irradiation dose per unit time, the scheduled X-ray irradiation period, the maximum exposure tolerance dose, and the minimum X-ray irradiation dose per unit time can also be computed using other information (imaging conditions, information on the subject, etc.) input from the input unit 110.

Figure 3A:
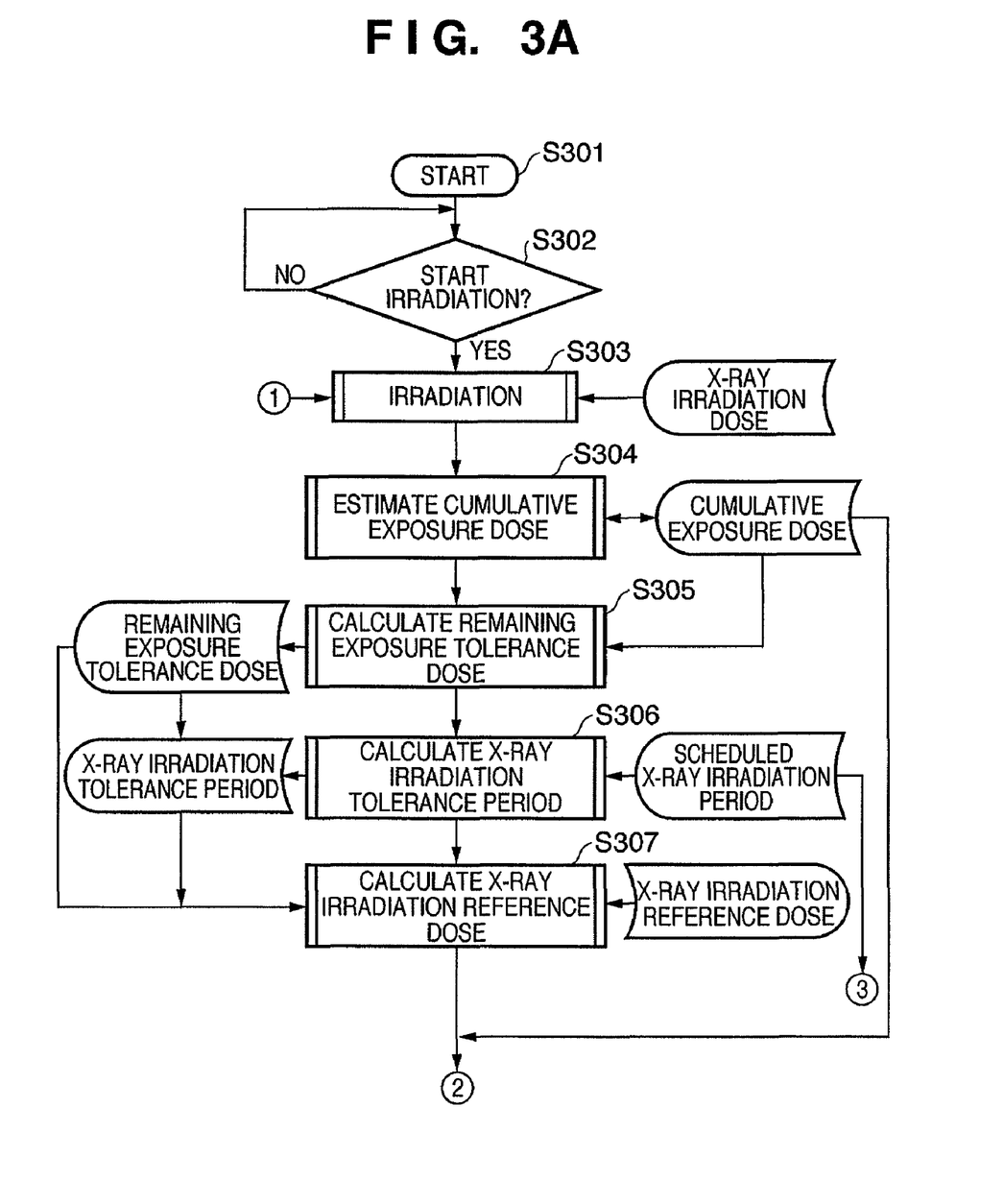
FIGS. 3A and 3B are flowcharts illustrating the operation flow of the X-ray imaging apparatus according to a first embodiment.
Figure 3B:
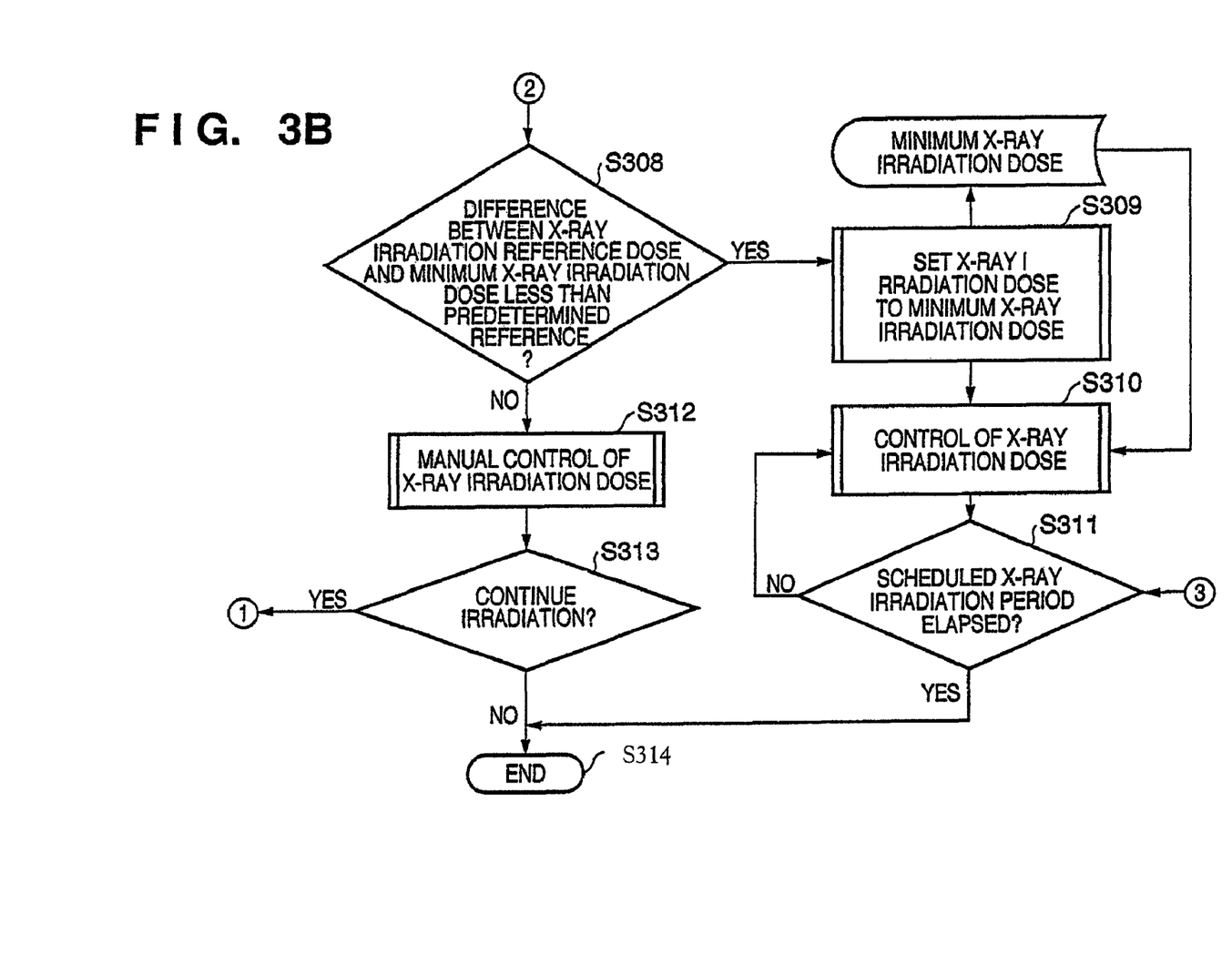

FIGS. 3A and 3B are flowcharts illustrating the operation flow of the X-ray imaging apparatus according to a first embodiment, with the operations of the steps being executed under the overall control of the CPU 201.

In step 301, the CPU 201 starts this process.

In step 302, the CPU 201 determines whether a trigger for starting irradiation has been input. A trigger for starting irradiation is, for example, detection of the foot pedal or the irradiation switch constituting the input unit 110 being depressed. If it is determined that a trigger for starting irradiation has been input (S302:YES), the CPU 201 allows the processing to proceed to step 303.

On the other hand, if it is determined that a trigger for starting irradiation has not been input (S302:NO), the processing returns to step 302 and enters a standby state such as polling standby or the like until a trigger for starting irradiation is given.

In step 303, the CPU 201 instructs the X-ray irradiation control unit 108 to control the X-ray generation unit 102. The X-ray generation unit 102 then performs X-ray irradiation at the X-ray irradiation dose per unit time held by the X-ray irradiation dose management unit 204.

In step 304, the CPU 201 executes the function of the cumulative exposure dose estimation unit 208. Specifically, the CPU 201 estimates (computes) the cumulative exposure dose, based on factors (tube voltage, mAs, filtration, FSD, apparatus, etc.) that affect the X-ray irradiation dose per unit time. The Non-Dosimeter Dosimetry (NDD) method can be utilized, for example.

In S305, the CPU 201 executes the function of the remaining exposure tolerance dose calculation unit 213, which functions as a remaining exposure tolerance dose computation unit. Specifically, the CPU 201 computes the remaining exposure tolerance dose E2 by subtracting the cumulative exposure dose E1 computed in S304 from the maximum exposure tolerance dose E3 held by the maximum exposure tolerance dose management unit 209.

In step 306, the CPU 201 executes the function of the X-ray irradiation tolerance period calculation unit 206. Specifically, the CPU 201 computes the X-ray irradiation tolerance period (T4−T0) by subtracting the actual irradiation period T0 at a prescribed time t1 from the scheduled X-ray irradiation period T4 held by the scheduled X-ray irradiation period management unit 205.

Figure 4:
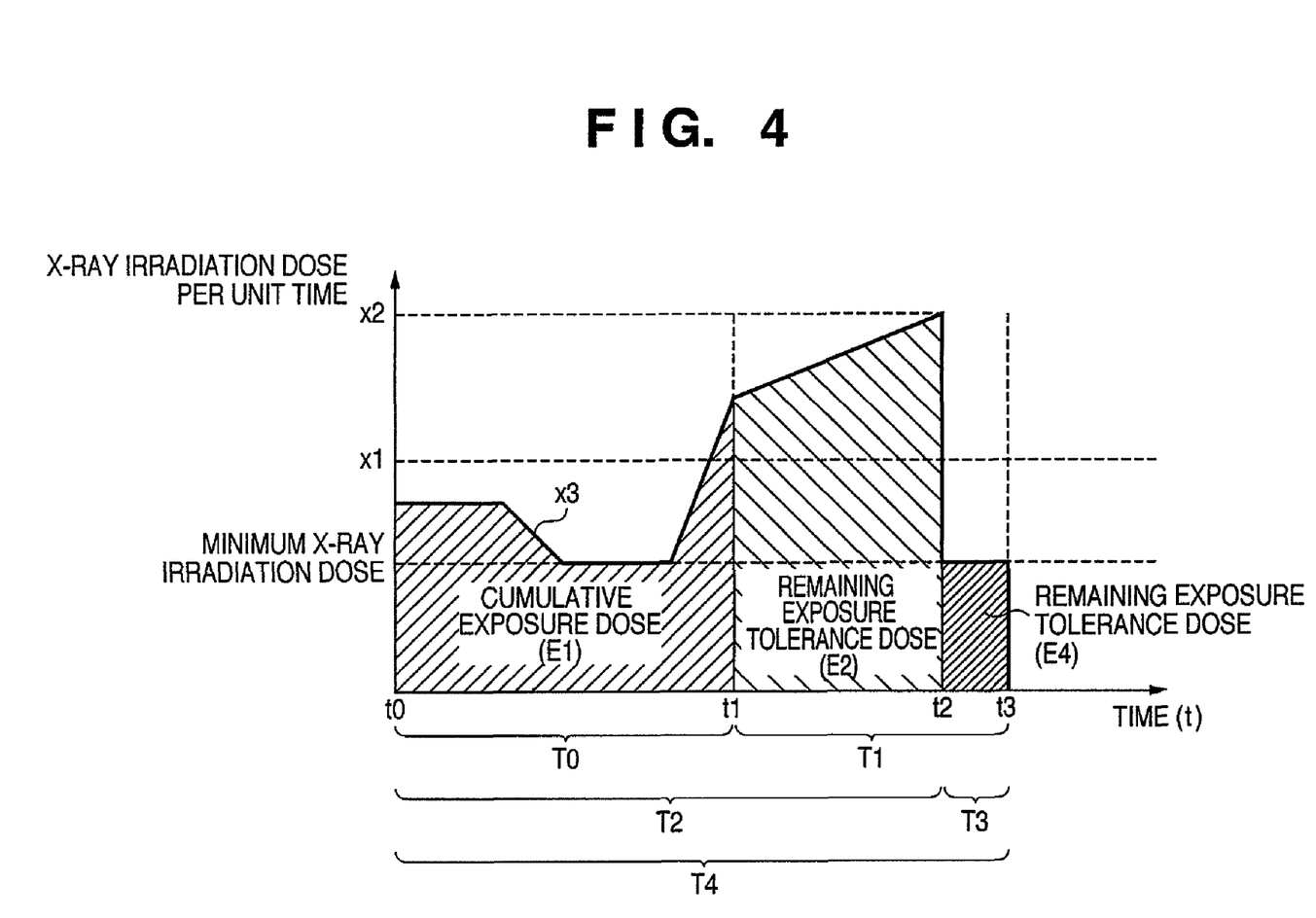
FIG. 4 illustrates an exemplary X-ray irradiation control in the first embodiment.

In step 307, the CPU 201 executes the function of the X-ray irradiation reference dose calculation unit 212. Specifically, the CPU 201 computes, based on the remaining exposure tolerance dose and the X-ray irradiation tolerance period, an X-ray irradiation reference dose per unit time at which the cumulative exposure dose will equal the remaining exposure tolerance dose in the case where X-rays are irradiated at a constant X-ray irradiation dose per unit time for the duration of the X-ray irradiation tolerance period. The X-ray irradiation reference dose per unit time computed here is, for example, x1 as shown in FIG. 4.

In step 308, the CPU 201 derives the difference between the X-ray irradiation reference dose per unit time computed in step 307 and the minimum X-ray irradiation dose per unit time held by the minimum X-ray irradiation dose management unit 207. If the difference value is less than a predetermined reference (S308:YES), the CPU 201 allows the processing to proceed to step 309.

In step 309, the CPU 201, functioning as a control unit, sets the minimum X-ray irradiation dose per unit time as the X-ray irradiation dose per unit time within the X-ray irradiation tolerance period.

In step 310, the X-ray control unit 211 controls the X-ray irradiation dose per unit time to be at the minimum X-ray irradiation dose set in step 309. The operator is thus unable to manually increase or decrease the X-ray irradiation dose per unit time. However, the operator will be able to complete the scheduled procedure by continuing the X-ray irradiation using the minimum X-ray irradiation dose per unit time required for the procedure.

In step 311, the scheduled X-ray irradiation period management unit 205 determines whether the held scheduled X-ray irradiation period T4 has elapsed. If the scheduled X-ray irradiation period T4 has elapsed (S311:YES), the processing proceeds to step 314 and is ended. If it is determined that the scheduled X-ray irradiation period T4 has not elapsed (S311:NO), the scheduled X-ray irradiation period management unit 205 returns the processing to S310 and continues the control using the minimum X-ray irradiation dose per unit time.

On the other hand, if it is determined in S308 that the difference value between the X-ray irradiation reference dose per unit time and the minimum X-ray irradiation dose is not less than the predetermined reference (S308:NO), the CPU 201 allows the processing to proceed to step 312. In step 312, the X-ray control unit 211 performs an X-ray control according to an X-ray irradiation per unit time set manually by the operator.

In step 313, the CPU 201 determines whether a trigger for irradiation is being given, such as the irradiation switch or the foot pedal being depressed. The CPU 201 determines to continue the irradiation if input of a trigger for irradiation is detected (S313:YES), whereupon the processing returns to step 303 and similar processing is repeated. On the other hand, if input of a trigger for irradiation is not detected by the CPU 201 in the determination in step 313, the CPU 201 determines to end the irradiation (S313:NO), whereupon the processing proceeds to step 314 and is ended.

FIG. 4 illustrates an exemplary X-ray irradiation control in the first embodiment. X-ray irradiation starts at time t0. x3 shows the X-ray irradiation dose per unit time actually irradiated onto the subject. This X-ray irradiation dose per unit time is managed by the X-ray irradiation dose management unit 204. The cumulative exposure dose E1 shows the cumulative value of the X-ray irradiation dose from the irradiation start time t0 until the execution time t1 of the X-ray irradiation reference dose calculation unit 212. The cumulative exposure dose estimation unit 208 can estimate (compute) the cumulative exposure dose E1 based on the history of the X-ray irradiation dose x3 per unit time.

T0 shows the period (t1–t0) from the irradiation start time t0 until the execution time t1 of the X-ray irradiation reference dose calculation unit 212. T4, which is the period required for the procedure, shows the scheduled X-ray irradiation period held by the scheduled X-ray irradiation period management unit 205. At the execution time t1 of the X-ray irradiation reference dose calculation unit 212, the X-ray irradiation reference dose calculation unit 212 computes the X-ray irradiation reference dose x1 per unit time. At time t1, the X-ray irradiation tolerance period calculation unit 206 computes the remaining exposure tolerance period T1. At time t1, the remaining exposure tolerance dose calculation unit 213 computes the remaining exposure dose tolerated for irradiation from time t1 (remaining exposure tolerance dose E2). The remaining exposure tolerance dose E2 can be computed based on equation (2).

The CPU 201 derives the difference between the computed X-ray irradiation reference dose per unit time and the minimum X-ray irradiation dose per unit time held by the minimum X-ray irradiation dose management unit 207. If the difference value is greater than or equal to a predetermined reference, the procedure can be continued using an X-ray irradiation dose set manually by the operator. This processing corresponds to S308:NO, S312, S313:YES and S303 in FIG. 3A. At time t1, the operator can continue the procedure based on an X-ray irradiation dose set manually, since the difference value is greater than or equal to the predetermined reference.

On the other hand, if the difference value is less than the predetermined reference, the CPU 201 sets the X-ray irradiation dose per unit time within the X-ray irradiation tolerance period to the minimum X-ray irradiation dose.

T2 shows the period (t2–t0) from the irradiation start time t0 until an execution time t2 of the X-ray irradiation reference dose calculation unit 212. At the execution time t2 of the X-ray irradiation reference dose calculation unit 212, the X-ray irradiation reference dose calculation unit 212 computes an X-ray irradiation reference dose x2 per unit time.

At time t2, the X-ray irradiation tolerance period calculation unit 206 computes the remaining exposure tolerance period T3. At time t2, the remaining exposure tolerance dose calculation unit 213 computes the remaining exposure dose tolerated for irradiation from time t2 (remaining exposure tolerance dose E4).

Assume that the difference between the X-ray irradiation reference dose x2 per unit time computed at time t2 and the minimum X-ray irradiation dose per unit time held by the minimum X-ray irradiation dose management unit 207 is less than the predetermined reference. In this case, the CPU 201 sets the X-ray irradiation dose per unit time within the X-ray irradiation tolerance period T3 to the minimum X-ray irradiation dose. The operator can continue the procedure until time t3 at the set X-ray irradiation dose per unit time (minimum X-ray irradiation dose).

The CPU 201 can control the period T0 from the irradiation start time t0 until the execution time t1 of the X-ray irradiation reference dose calculation unit 212, and the period T2 from time t0 until time t2.

The present embodiment enables X-ray irradiation to be continued until a time period set by the operator elapses, at the same time as inhibiting the excessive irradiation of X-rays onto the subject.

Second Embodiment

Figure 5A:
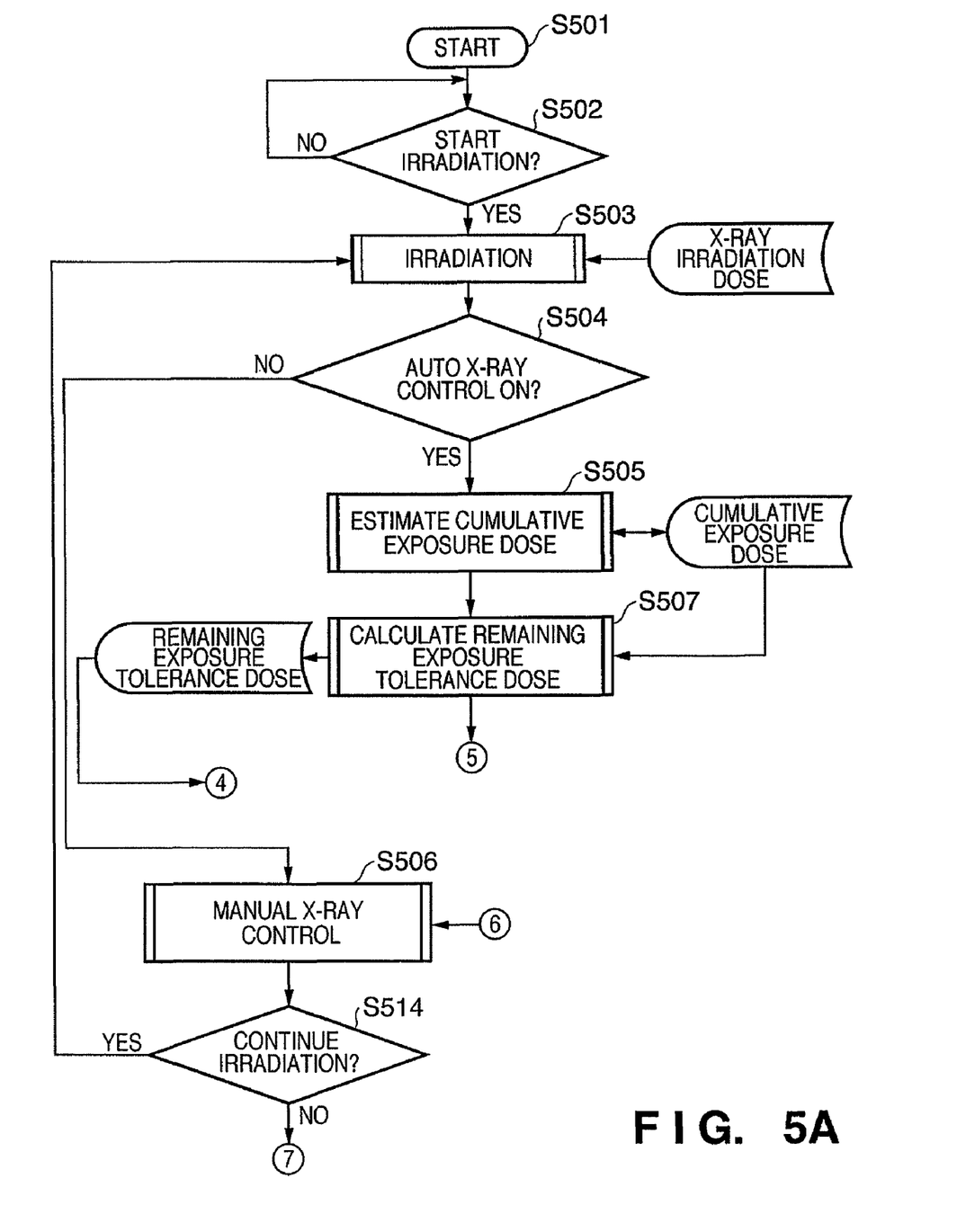
FIGS. 5A and 5B are flowcharts illustrating the operation flow of the X-ray imaging apparatus according to a second embodiment.
Figure 5B:
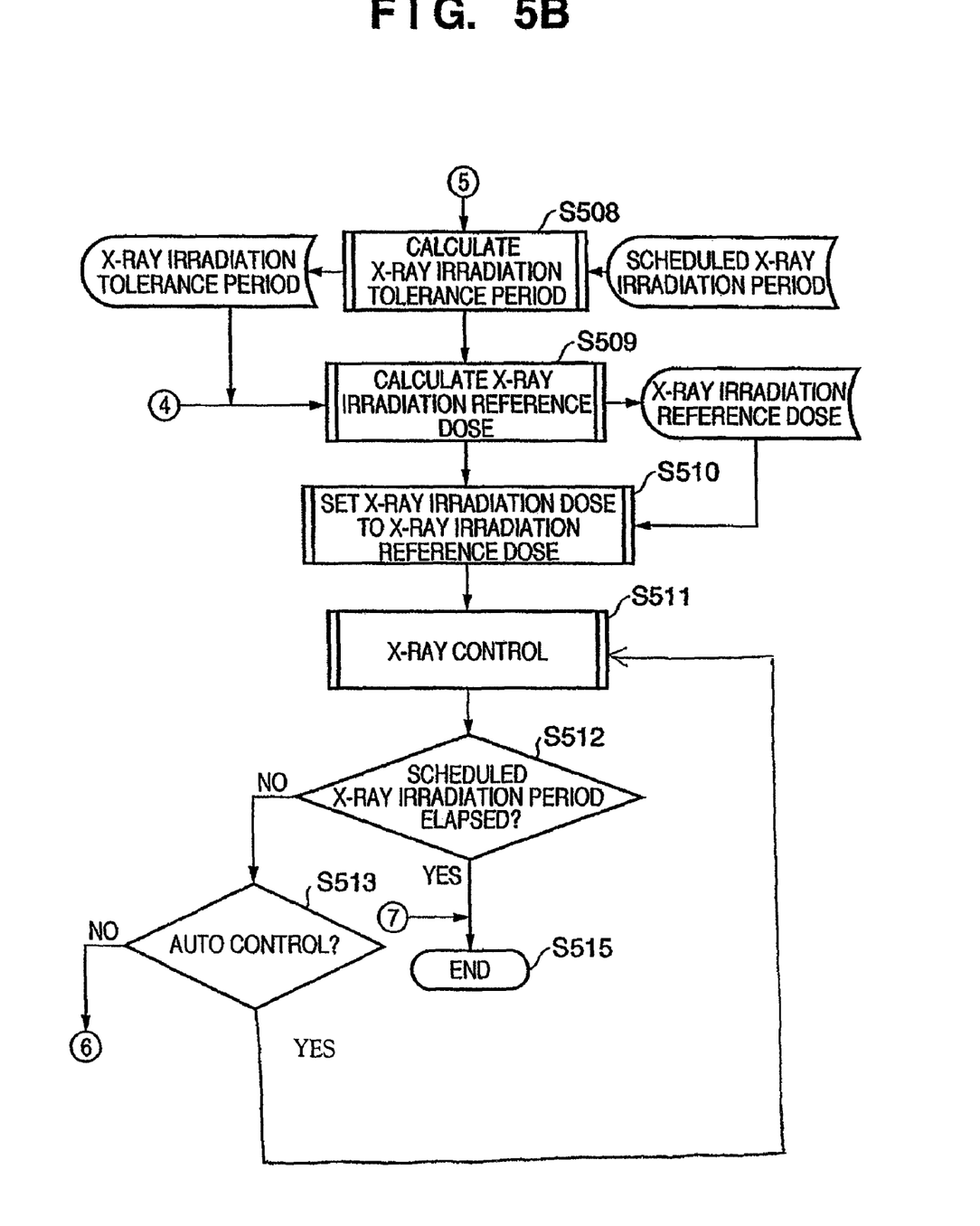

FIGS. 5A and 5B are flowcharts illustrating the operation flow of the X-ray imaging apparatus according to a second embodiment, with the operations of the steps being executed under the overall control of the CPU 201. The X-ray imaging apparatus is assumed to have a similar configuration to FIGS. 1 and 2 described in the first embodiment.

In step 501, the CPU 201 starts this process.

In step 502, the CPU 201 determines whether a trigger for starting irradiation has been input. In step 503, the X-ray generation unit 102 performs X-ray irradiation based on the X-ray irradiation dose per unit time held by the X-ray irradiation dose management unit 204.

In step 504, the CPU 201 determines whether to set the X-ray irradiation dose per unit time manually or automatically (auto X-ray control), based on a selection operation by the operator. If auto X-ray control is instructed by the operation of the operator (S504:YES), the processing proceeds to step 505.

In step 505, the cumulative exposure dose estimation unit 208 estimates (computes) the cumulative exposure dose, based on factors (tube voltage, mAs, filtration, FSD, apparatus, etc.) that affect the X-ray irradiation dose per unit time.

In S507, the CPU 201 executes the function of the remaining exposure tolerance dose calculation unit 213, which functions as a remaining exposure tolerance dose computation unit. Specifically, the CPU 201 computes the remaining exposure tolerance dose E2 by subtracting the cumulative exposure dose E1 computed in S505 from the maximum exposure tolerance dose E3 held by the maximum exposure tolerance dose management unit 209.

In step 508, the CPU 201 executes the function of the X-ray irradiation tolerance period calculation unit 206. Specifically, the CPU 201 computes the X-ray irradiation tolerance period (T4−T0=T1), as the function of the X-ray irradiation tolerance period calculation unit 206, by subtracting the irradiation period T0 actually irradiated at the prescribed time t1 from the scheduled X-ray irradiation period (T4) held by the function of the scheduled X-ray irradiation period management unit 205.

In step 509, the CPU 201 computes an X-ray irradiation reference dose per unit time based on the remaining exposure tolerance dose and the X-ray irradiation tolerance period, as the function of the X-ray irradiation reference dose calculation unit 212. Specifically, the CPU 201 computes, as an X-ray irradiation reference dose, a constant X-ray irradiation dose per unit time at which the cumulative exposure dose will equal the remaining exposure tolerance dose in the case where irradiation is continued at a constant X-ray irradiation dose per unit time. The X-ray irradiation reference dose per unit time computed here is, for example, x1 in FIG. 6.

In step 510, the CPU 201 sets the X-ray irradiation reference dose per unit time computed in step 509 as the X-ray irradiation dose per unit time.

In step 511, the X-ray control unit 211 controls the X-ray irradiation with the X-ray irradiation reference dose per unit time set in step 510.

In step 512, the scheduled X-ray irradiation period management unit 205 determines whether the scheduled X-ray irradiation period T4 has elapsed. If the scheduled X-ray irradiation period management unit 205 has determined that the scheduled X-ray irradiation period (T4) has elapsed (S512:YES), the processing proceeds to step 514 and is ended. If the scheduled X-ray irradiation period management unit 205 has determined that the scheduled X-ray irradiation period (T4) has not elapsed (S512:NO), the processing proceeds to S513. In the case of continuing the control (S513:YES), the processing returns to S511, where the control is continued based on the set X-ray irradiation dose per unit time.

On the other hand, if in step 513 auto X-ray control is not instructed by the operator (S513:NO), the processing proceeds to S506.

In step 506, the CPU 201 executes the function of the X-ray control unit 211, and performs X-ray control according to an X-ray irradiation dose per unit time set manually by the operator.

In step 514, the CPU 201 determines whether a trigger for irradiation is being given, such as the irradiation switch or the foot pedal being depressed. The CPU 201 determines to continue the irradiation if input of a trigger for irradiation is detected (S514:YES), whereupon the processing returns to step 503 and similar processing is repeated. On the other hand, if input of a trigger for irradiation is not detected by the CPU 201 in the determination of step 514, the CPU 201 determines to end the irradiation (S514:NO), whereupon the processing proceeds to step 515 and is ended.

Figure 6:
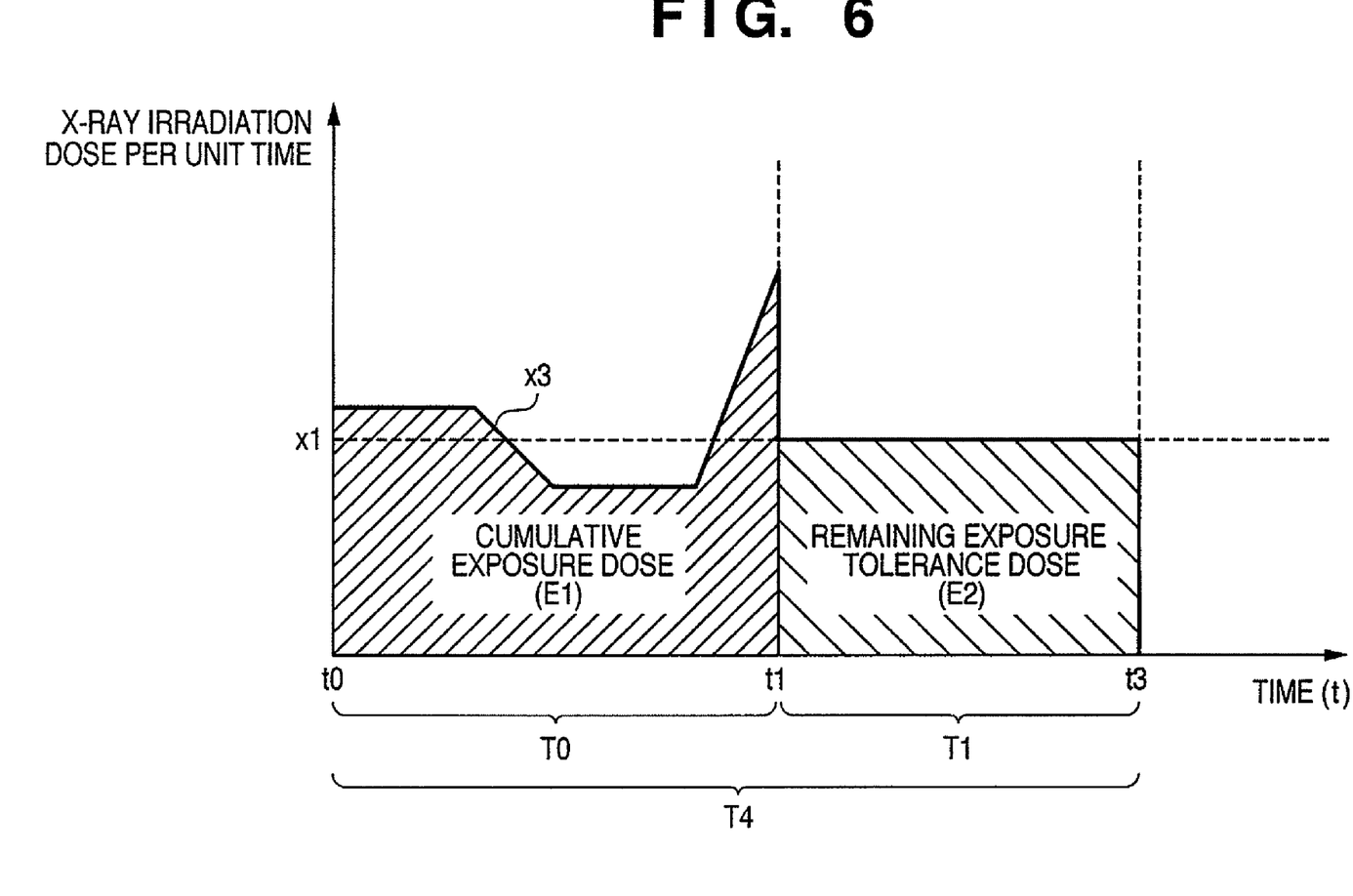
FIG. 6 illustrates an exemplary X-ray irradiation control in the second embodiment.

FIG. 6 illustrates an exemplary X-ray irradiation control in the second embodiment. X-ray irradiation starts at time t0. Time t1 is when the X-ray control is instructed (selected) by the operator, and also the execution time of the X-ray irradiation reference dose calculation unit 212. x3 shows the X-ray irradiation dose per unit time actually irradiated onto the subject. The cumulative exposure dose E1 shows the cumulative value of the X-ray exposure dose from the irradiation start time t0 until the execution time t1 of the X-ray irradiation reference dose calculation unit 212. Executing the function of the cumulative exposure dose estimation unit 208 enables the cumulative exposure dose E1 to be estimated (computed) based on the history of the X-ray irradiation dose per unit time x3.

T0 shows the period (t1−t0) from the X-ray irradiation start time t0 until the execution time t1 of the X-ray irradiation reference dose calculation unit 212. T4, which is the period required for the procedure, shows the scheduled X-ray irradiation period held by the scheduled X-ray irradiation period management unit 205. t3 shows the scheduled X-ray irradiation period end time held by the scheduled X-ray irradiation period management unit 205.

At the execution time t1 of the X-ray irradiation reference dose calculation unit 212, the CPU 201 computes the X-ray irradiation reference dose x1 per unit time. At time t1, the CPU 201 computes the remaining X-ray irradiation tolerance period T1 by executing the function of the X-ray irradiation tolerance period calculation unit 206. At time t1, the CPU 201 computes the remaining exposure dose tolerated for irradiation from time t1 (remaining exposure tolerance dose E2) by executing the function of the remaining exposure tolerance dose calculation unit 213. The remaining exposure tolerance dose can be computed based on equation (2).

If auto control is selected (corresponds to S504:YES in FIG. 5A), the CPU 201 sets the X-ray irradiation dose per unit time within the X-ray irradiation tolerance period T1 to the X-ray irradiation reference dose x1. The operator can continue the procedure until time t3, based on the set X-ray irradiation dose (X-ray irradiation reference dose x1).

The present embodiment enables X-ray irradiation to be continued until a time period set by the operator elapses, at the same time as inhibiting the excessive irradiation of X-rays onto the subject.

Third Embodiment

Figure 7A:
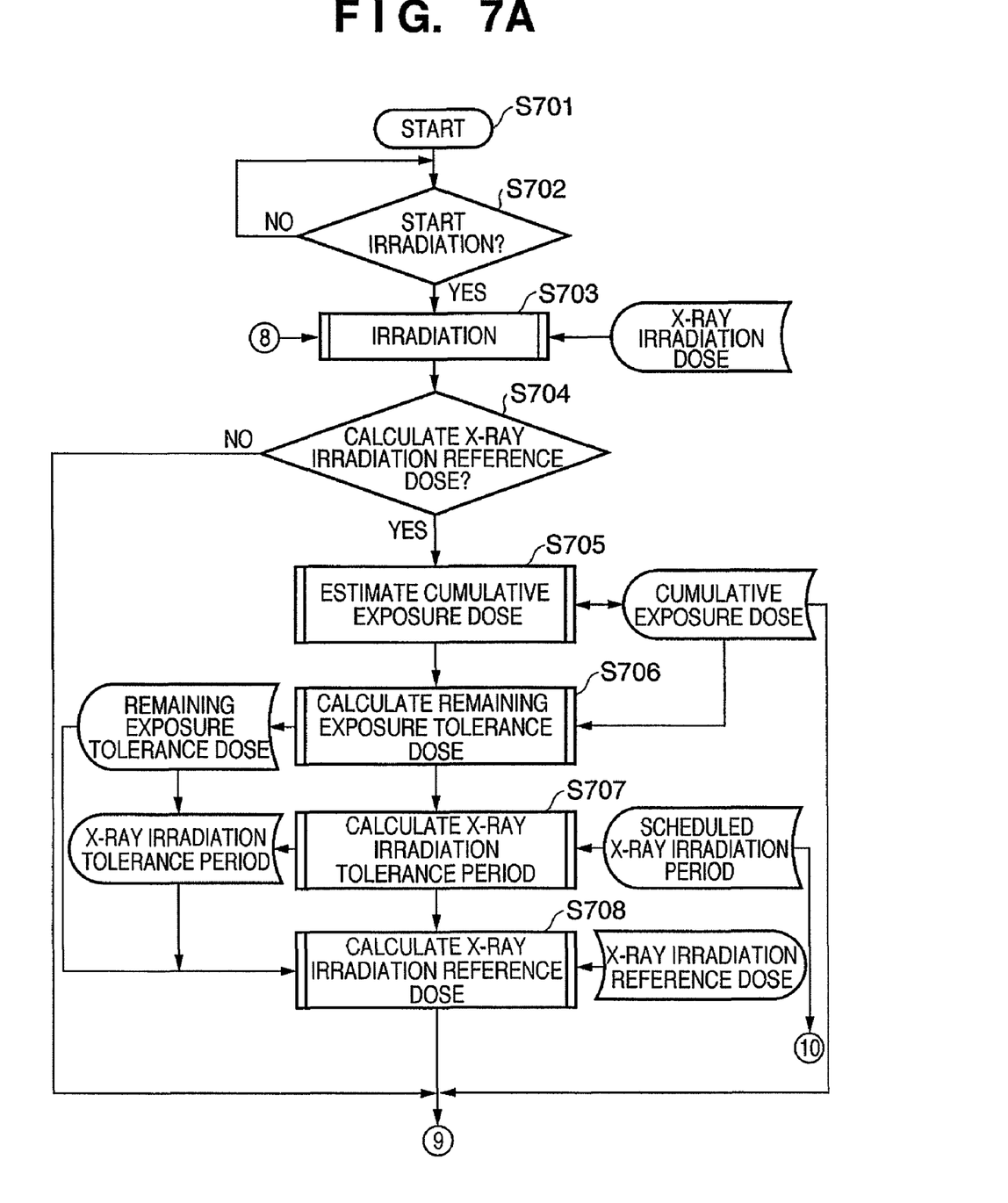
FIGS. 7A and 7B are flowcharts illustrating the operation flow of the X-ray imaging apparatus according to a third embodiment.
Figure 7B:
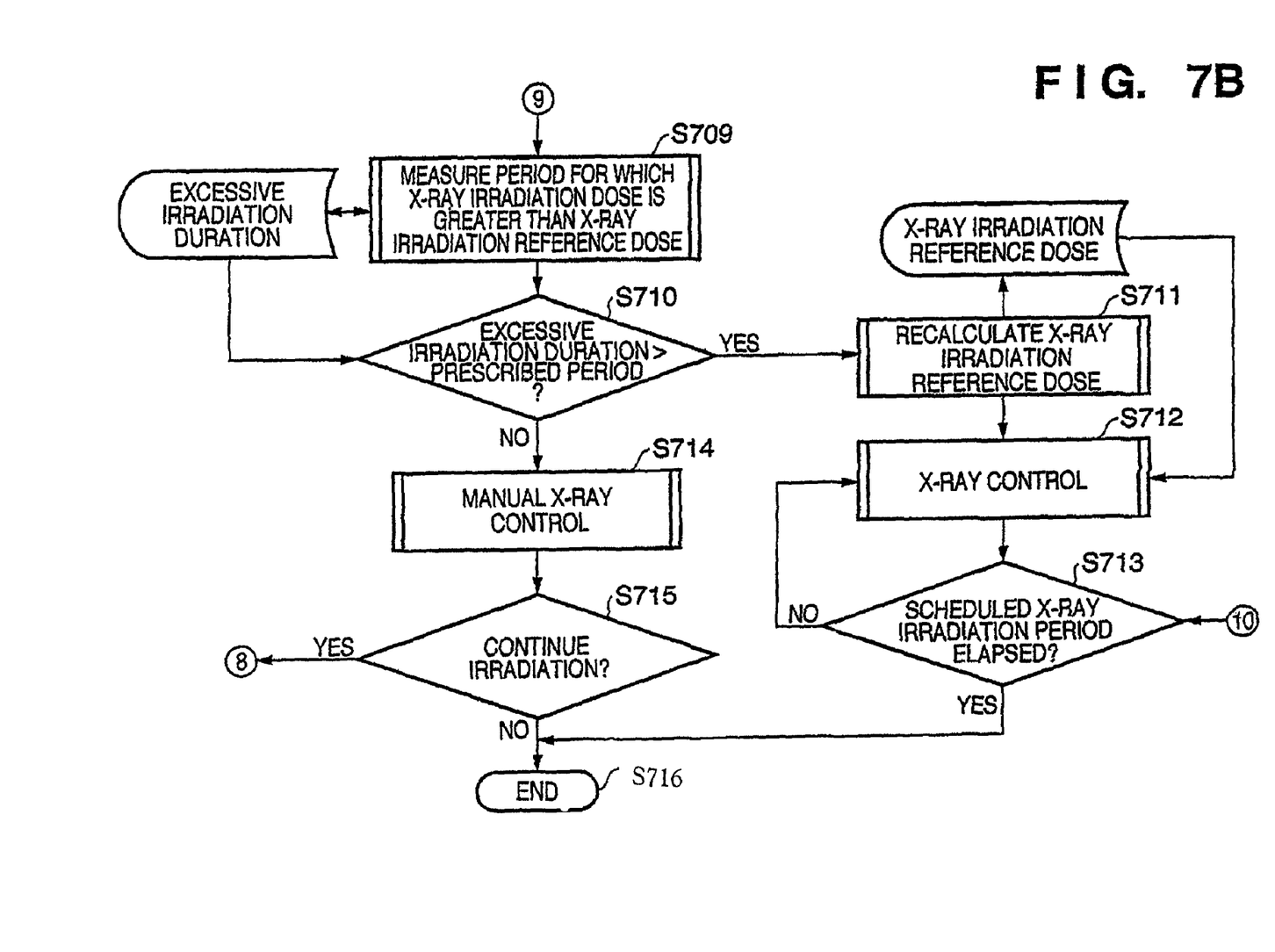

FIGS. 7A and 7B are flowcharts illustrating the operation flow of the X-ray imaging apparatus according to a third embodiment, with the operations of the steps being executed under the overall control of the CPU 201. The X-ray imaging apparatus is assumed to have a similar configuration to FIGS. 1 and 2 described in the first embodiment.

In step 701, the CPU 201 starts this process.

In step 702, the CPU 201 determines whether a trigger signal for starting irradiation has been input. In step 703, the X-ray generation unit 102 performs X-ray irradiation based on the X-ray irradiation dose per unit time held by the X-ray irradiation dose management unit 204.

In step 704, the CPU 201 determines whether an instruction for calculation of the X-ray irradiation reference dose per unit time has been given. If an instruction for calculation of the X-ray irradiation reference dose per unit time has been given (S704:YES), the processing proceeds to step 705.

On the other hand, if it is determined in S704 that an instruction for calculation of the X-ray irradiation reference dose per unit time has not been given (S704:NO), the processing proceeds to step 709.

The instruction to calculate the X-ray irradiation reference dose per unit time may be given by an operator input from the input unit 110, or can also be input periodically using the timer 250.

In step 705, the CPU 201 executes the function of the cumulative exposure dose estimation unit 208. Specifically, the CPU 201 estimates (computes) the cumulative exposure dose, based on factors (tube voltage, mAs, filtration, FSD, apparatus, etc.) that affect the X-ray irradiation dose per unit time.

In S706, the CPU 201 executes the function of the remaining exposure tolerance dose calculation unit 213, which functions as a remaining exposure tolerance dose computation unit. Specifically, the CPU 201 computes the remaining exposure tolerance dose E2 by subtracting the cumulative exposure dose E1 computed at S705 from the maximum exposure tolerance dose E3 held by the maximum exposure tolerance dose management unit 209.

In step 707, the CPU 201 executes the function of the X-ray irradiation tolerance period calculation unit 206. Specifically, the CPU 201 computes the X-ray irradiation tolerance period (T4−T0=T1) by subtracting the actual irradiation period (T0) at a prescribed time t1 from the scheduled X-ray irradiation period (T4) held by the scheduled X-ray irradiation period management unit 205.

In step 708, the CPU 201 executes the function of the X-ray irradiation reference dose calculation unit 212. Specifically, the CPU 201 computes, as an X-ray irradiation reference dose, a constant X-ray irradiation dose per unit time at which the cumulative exposure dose will equal the remaining exposure tolerance dose in the case where X-ray irradiation is continued at a constant X-ray irradiation dose per unit time for the duration of the X-ray irradiation tolerance period, based on the remaining exposure tolerance dose and the X-ray irradiation tolerance period.

In step 709, the CPU 201 measures the period for which the current X-ray irradiation dose per unit time held by the X-ray irradiation dose management unit 204 continuously exceeds the X-ray irradiation reference dose per unit time computed in S708 (excessive irradiation duration). The CPU 201 can measure time by using the timer 250.

In step 710, the CPU 201 determines whether the excessive irradiation duration measured in step 709 has exceeded a prescribed period (e.g., 10 min.). If the excessive irradiation duration has exceeded the prescribed period (S710:YES), the processing proceeds to step S711. On the other hand, if the excessive irradiation duration has not exceeded the prescribed period (S710:NO), the processing proceeds to step S714.

In step 711, the CPU 201 executes the function of the cumulative exposure dose estimation unit 208. Specifically, the CPU 201, functioning as an estimation unit, re-estimates (computes) the cumulative exposure dose of X-rays irradiated onto the subject (object) 105.

The CPU 201 executes the function of the remaining exposure tolerance dose calculation unit 213. Specifically, the CPU 201, functioning as a remaining exposure tolerance dose computation unit, re-computes the remaining exposure tolerance dose, using the difference between the maximum exposure tolerance dose E3 and the re-estimated cumulative exposure dose.

The CPU 201 executes the function of the X-ray irradiation tolerance period calculation unit (X-ray irradiation tolerance period computation unit) 206. Specifically, the CPU 201 re-computes the X-ray irradiation tolerance period based on the difference between the scheduled X-ray irradiation period and the irradiation period for which X-rays have actually been irradiated.

The CPU 201 executes the function of the X-ray irradiation reference dose calculation unit (X-ray irradiation reference dose computation unit) 212. Specifically, the CPU 201 re-computes the X-ray irradiation reference dose per unit time that forms a basis of the X-ray irradiation, based on the recalculated remaining exposure tolerance dose and the recalculated X-ray irradiation tolerance period.

The CPU 201 then executes the function of the X-ray irradiation dose management unit 204. Specifically, the CPU 201 sets and holds the recalculated X-ray irradiation reference dose per unit time. This processing corresponds to S705 to S708 in FIG. 7A.

In step 712, the CPU 201, specifically, sets the X-ray irradiation reference dose per unit time set in step 711 as the X-ray irradiation dose per unit time.

In step 713, the CPU 201 executes the function of the scheduled X-ray irradiation period management unit 205. Specifically, the CPU 201 determines whether the scheduled X-ray irradiation period (T4) has elapsed. If the scheduled X-ray irradiation period management unit 205 has determined that the scheduled X-ray irradiation period (T4) has elapsed (S713:YES), the processing proceeds to step 716 and is ended.

On the other hand, if it is determined that the scheduled X-ray irradiation period (T4) has not elapsed (S713:NO), the processing returns to S712 and X-ray irradiation based on X-ray irradiation reference dose per unit time is continued until the scheduled X-ray irradiation period expires.

If it is determined in S710 that the excessive irradiation duration has not exceeded the prescribed period (S710:NO), the CPU 201 in step 714 executes the function of the X-ray control unit 211, and controls the X-ray irradiation with an X-ray irradiation dose per unit time set manually by the operator.

In step 715, the CPU 201 determines whether a trigger signal for irradiation is being given, such as the irradiation switch or the foot pedal being depressed. The CPU 201 determines to continue the irradiation if input of a trigger signal for irradiation is detected (S715:YES), whereupon the processing returns to step 703 and similar processing is repeated. On the other hand, if input of a trigger signal for irradiation is not detected by the CPU 201 in the determination of step 715, the CPU 201 determines to end the irradiation (S715:NO), whereupon the processing proceeds to step 716 and is ended.

Figure 8:
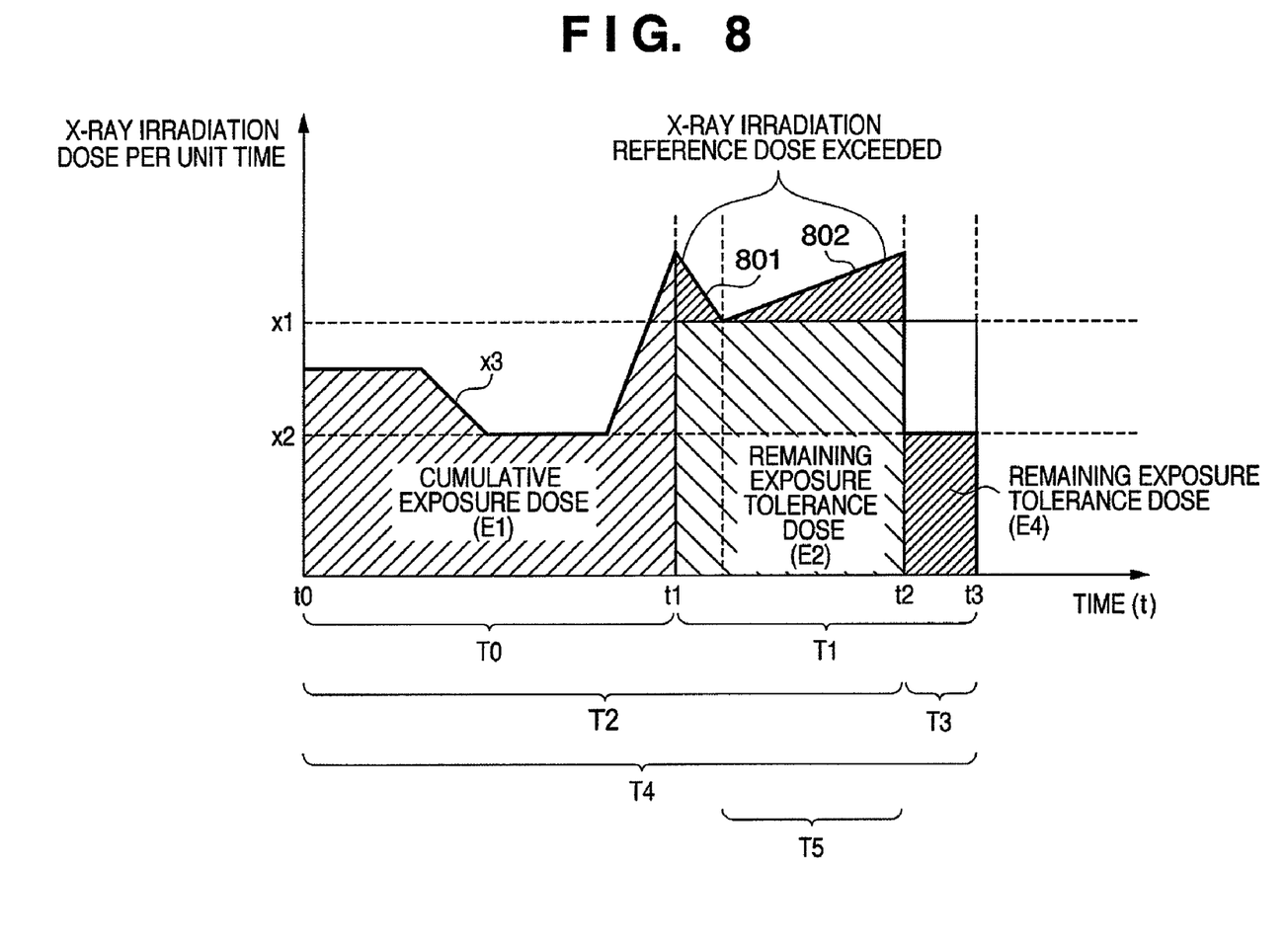
FIG. 8 illustrates an exemplary X-ray irradiation control in the third embodiment.

FIG. 8 illustrates an exemplary X-ray irradiation control in the third embodiment. X-ray irradiation starts at time t0. x3 shows the X-ray irradiation dose per unit time actually irradiated onto the subject (object) 105. This X-ray irradiation dose per unit time is managed by the X-ray irradiation dose management unit 204. The cumulative exposure dose E1 shows the cumulative value of the X-ray irradiation dose from the irradiation start time t0 until the execution time t1 of the X-ray irradiation reference dose calculation unit 212 (i.e. the area under the line x3). The CPU 201 can estimate (compute) the cumulative exposure dose E1 based on the history of the X-ray irradiation dose x3 per unit time, by executing the function of the cumulative exposure dose estimation unit 208.

T0 shows the period (t1−t0) from the irradiation start time t0 until the execution time t1 of the X-ray irradiation reference dose calculation unit 212. T4, which is the period required for the procedure, shows the scheduled X-ray irradiation period held by the scheduled X-ray irradiation period management unit 205. t3 shows the scheduled X-ray irradiation period end time.

At time t1, the CPU 201 computes the X-ray irradiation reference dose x1 for controlling the X-ray irradiation dose per unit time from time t1, by executing the function of the X-ray irradiation reference dose calculation unit 212.

At time t1, the CPU 201 computes the remaining exposure tolerance period T1, by executing the function of the X-ray irradiation tolerance period calculation unit 206. At time t1, the remaining exposure tolerance dose calculation unit 213 computes the remaining exposure tolerance dose E2 tolerated for irradiation from time t1. The remaining exposure tolerance dose can be computed based on equation (2).

In FIG. 8, areas 801 and 802 indicate where the X-ray irradiation dose per unit time exceeded the X-ray irradiation reference dose x1. The CPU 201 can detect when a continuous prescribed reference period (T5: excessive irradiation period) has elapsed in a state where the X-ray irradiation reference dose x1 per unit time is exceeded, based on the time measurement of the timer 250. T2 shows the period from the irradiation start time t0 until the execution time t2 of the X-ray irradiation reference dose calculation unit 212.

At the execution time t2, which is the time at which the excessive irradiation period T5 elapses, the CPU 201 activates the cumulative exposure dose estimation unit 208, the remaining exposure tolerance dose calculation unit 213, the X-ray irradiation tolerance period calculation unit 206, and the X-ray irradiation reference dose calculation unit 212. Then, the cumulative exposure dose, the remaining irradiation tolerance dose, the X-ray irradiation tolerance period and the X-ray irradiation reference dose per unit time are recomputed in accordance with the processing of S705 to S708 illustrated in FIG. 7A.

If it is detected that the continuous prescribed reference period (T5: excessive irradiation period) has elapsed in a state where the X-ray irradiation reference dose x1 per unit time is exceeded, the CPU 201 can issue a warning indicating excessive irradiation to the operator.

In FIG. 8, the CPU 201, functioning as the X-ray irradiation reference dose calculation unit 212, computes an X-ray irradiation reference dose x2 per unit time at the execution time t2, which is the time at which the excessive irradiation period T5 elapses. At time t2, the CPU 201, functioning as the X-ray irradiation tolerance period calculation unit 206, computes a remaining X-ray irradiation tolerance period T3. Also at time t2, the CPU 201, functioning as the remaining exposure tolerance dose calculation unit 213, calculates a remaining exposure tolerance dose E4 tolerated for radiation from time t2. The CPU 201 sets the X-ray irradiation dose per unit time within the remaining X-ray irradiation tolerance period T3 to the X-ray irradiation reference dose x2. The operator is able to continue the procedure until time t3, based on the set X-ray irradiation dose (X-ray irradiation reference dose x2).

The present embodiment enables X-ray irradiation to be continued until a time period set by the operator elapses, at the same time as inhibiting the excessive irradiation of X-rays onto the subject.

Also, the present embodiment enables excessive irradiation to be inhibited by warning the operator through issuing a warning indicating excessive irradiation in the case where X-ray irradiation is performed for longer than a prescribed period at an X-ray irradiation dose exceeding an X-ray irradiation reference dose per unit time.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-122802, filed May 7, 2007 which is hereby incorporated by reference herein in its entirety.

What is claimed is:

1. An X-ray imaging apparatus comprising:
   an estimation unit adapted to estimate a cumulative exposure dose of X-rays irradiated onto an object;
   a remaining exposure tolerance dose calculation unit adapted to calculate a remaining exposure tolerance dose, using a difference between a tolerated maximum exposure dose and the cumulative exposure dose;
   an X-ray irradiation tolerance period calculation unit adapted to calculate an X-ray irradiation tolerance period, using a difference between a predetermined scheduled X-ray irradiation period and an actual irradiation period of X-rays irradiated onto the object;
   an X-ray irradiation reference dose calculation unit adapted to calculate an X-ray irradiation reference dose per unit time that will form a basis of X-ray irradiation, based on the remaining exposure tolerance dose and the X-ray irradiation tolerance period; and
   a control unit adapted to control X-ray irradiation onto the object by setting an X-ray irradiation dose per unit time within the X-ray irradiation tolerance period, based on the X-ray irradiation reference dose,
   wherein when the difference between the X-ray irradiation reference dose per unit time and a minimum X-ray irradiation dose per unit time required is less than a predetermined reference, the control unit sets an X-ray irradiation dose per unit time within the X-ray irradiation tolerance period to the minimum X-ray irradiation dose per unit time.

2. The X-ray imaging apparatus according to claim 1, further comprising a selection unit operable to select whether to set an X-ray irradiation does per unit time manually or automatically,
   wherein the control unit sets an X-ray irradiation dose per unit time within the X-ray irradiation tolerance period to the X-ray irradiation reference dose per unit time, when the automatic setting is selected.

3. The X-ray imaging apparatus according to claim 1, further comprising:
   a measurement unit adapted to measure an excessive irradiation duration for which the X-ray irradiation reference dose per unit time is continuously exceeded; and
   a warning unit adapted to issue a warning indicating excessive irradiation, when the excessive irradiation duration exceeds a predetermined reference period.

4. The X-ray imaging apparatus according to claim 3, wherein when the excessive irradiation duration exceeds the predetermined reference period,
   the estimation unit re-estimates a cumulative exposure dose of X-rays irradiated onto the object,
   the remaining exposure tolerance dose calculation unit recalculates a remaining exposure tolerance dose, using the difference between the maximum exposure dose and the re-estimated cumulative exposure dose,
   the X-ray irradiation tolerance period calculation unit re-calculates an X-ray irradiation tolerance period, using the difference between the scheduled X-ray irradiation period and the actual irradiation period of X-rays,
   the X-ray irradiation reference dose calculation unit re-calculates an X-ray irradiation reference dose per unit time that will form a basis of X-ray irradiation, based on the recalculated remaining exposure tolerance dose and the recalculated X-ray irradiation tolerance period, and
   the control unit sets an X-ray irradiation dose per unit time within the recalculated X-ray irradiation tolerance period to the recalculated X-ray irradiation reference dose per unit time.

* * * * *